(12) United States Patent
Mansfield et al.

(10) Patent No.: US 10,314,942 B2
(45) Date of Patent: Jun. 11, 2019

(54) MANUFACTURE OF BIOMATERIAL IMPLANTS VIA THREE-DIMENSIONAL PRINTING TECHNOLOGY

(71) Applicant: Bacterin International, Inc., Belgrade, MT (US)

(72) Inventors: Michael Mansfield, Bozeman, MT (US); Daniel Cox, Belgrade, MT (US)

(73) Assignee: BACTERIN INTERNATIONAL, INC., Belgrade, MT (US)

( * ) Notice: Subject to any disclaimer, the term of this patent is extended or adjusted under 35 U.S.C. 154(b) by 325 days.

(21) Appl. No.: 14/755,931

(22) Filed: Jun. 30, 2015

(65) Prior Publication Data
US 2015/0374450 A1    Dec. 31, 2015

Related U.S. Application Data

(60) Provisional application No. 62/019,371, filed on Jun. 30, 2014.

(51) Int. Cl.
| | | |
|---|---|---|
| *A61L 27/36* | (2006.01) | |
| *B29C 64/10* | (2017.01) | |
| *A61F 2/28* | (2006.01) | |
| *B33Y 80/00* | (2015.01) | |
| *A61F 2/30* | (2006.01) | |
| *B29C 64/165* | (2017.01) | |
| *B33Y 10/00* | (2015.01) | |

(52) U.S. Cl.
CPC ............ *A61L 27/3608* (2013.01); *A61F 2/28* (2013.01); *A61F 2/30942* (2013.01); *A61L 27/3604* (2013.01); *B29C 64/165* (2017.08); *B33Y 80/00* (2014.12); *A61F 2/2875* (2013.01); *A61F 2002/30948* (2013.01); *A61F 2002/30957* (2013.01); *A61F 2002/30962* (2013.01); *A61F 2240/002* (2013.01); *A61F 2310/00359* (2013.01); *A61F 2310/00365* (2013.01); *A61F 2310/00371* (2013.01); *A61L 2430/02* (2013.01); *B33Y 10/00* (2014.12)

(58) Field of Classification Search
CPC ............................. A61F 2/28; A61F 2/30942
USPC ................................... 264/239, 250
See application file for complete search history.

(56) References Cited

U.S. PATENT DOCUMENTS

| | | | |
|---|---|---|---|
| 5,314,476 A | 5/1994 | Prewett et al. | |
| 5,768,134 A * | 6/1998 | Swaelens | A61C 13/0004 433/201.1 |
| 6,280,478 B1 * | 8/2001 | Richter | A61F 2/28 623/23.56 |
| 6,530,958 B1 * | 3/2003 | Cima | A61F 2/022 623/23.51 |
| 7,001,551 B2 * | 2/2006 | Meredith | A61B 17/866 264/101 |
| 7,747,305 B2 | 6/2010 | Dean et al. | |
| 8,574,825 B2 | 11/2013 | Shelby et al. | |
| 2003/0006534 A1 * | 1/2003 | Taboas | A61F 2/30756 264/401 |
| 2012/0041094 A1 * | 2/2012 | Oral | A61L 27/16 522/75 |
| 2012/0251980 A1 * | 10/2012 | Bassett | A61C 8/0012 433/201.1 |

(Continued)

*Primary Examiner* — Cachet I Sellman
(74) *Attorney, Agent, or Firm* — Sheridan Ross P.C.

(57) ABSTRACT

The present invention relates to the manufacture of shaped biomaterial-based implants via three-dimensional printing technology.

25 Claims, 2 Drawing Sheets

(56) References Cited

U.S. PATENT DOCUMENTS

| | | | |
|---|---|---|---|
| 2013/0110470 A1* | 5/2013 | Vanasse | A61F 2/30942 |
| | | | 703/1 |
| 2013/0310364 A1* | 11/2013 | Li | C07D 401/14 |
| | | | 514/210.21 |
| 2014/0025181 A1 | 1/2014 | Vanasse et al. | |
| 2014/0314822 A1* | 10/2014 | Carter | A61L 27/3687 |
| | | | 424/423 |
| 2015/0037385 A1* | 2/2015 | Shah | A61L 27/46 |
| | | | 424/422 |
| 2015/0054195 A1* | 2/2015 | Greyf | B29C 67/0081 |
| | | | 264/250 |
| 2015/0073562 A1* | 3/2015 | Landon | A61F 2/389 |
| | | | 623/20.34 |
| 2015/0251361 A1 | 9/2015 | Meyer et al. | |

* cited by examiner

MANUFACTURE OF BIOMATERIAL IMPLANTS VIA THREE-DIMENSIONAL PRINTING TECHNOLOGY

CROSS REFERENCE TO RELATED APPLICATIONS

This application claims priority and the benefit under 35 U.S.C. § 119(e) to U.S. Provisional Patent Application Ser. No. 62/019,371 filed on Jun. 30, 2014, which is incorporated herein in its entirety by reference.

FIELD OF THE INVENTION

The present embodiments generally relate to methods for the three-dimensional printing manufacture of shaped biomaterial-based implants.

DESCRIPTION OF THE PRIOR ART

Methods for three-dimensional printing manufacturing of shaped products are known in the prior art. The use of biomaterials such as allograft tissue in three-dimensional printers is limited by factors such as curing temperatures and the form of the raw material input. A need remains for a facile method of generating shaped, biomaterial-based products for subsequent patient implantation.

U.S. Pat. No. 6,530,958 entitled "Tissue Regeneration Matrices By Solid Free-Form Fabrication Techniques," which is incorporated by reference in its entirety, discloses methods for formulated devices for tissue regeneration using computer-aided design in combination with solid free-form fabrication technology. U.S. Patent Publication No. 2014/0025181 entitled "Metallic Structures Having Porous Regions From Imaged Bone At Pre-Defined Anatomic Locations," which is incorporated by reference in its entirety, discloses metallic structures with porous regions to represent the architecture of bone. Methods for imaging bone at pre-defined anatomic locations to create the implants are also disclosed. U.S. Pat. No. 7,747,305 entitled "Computer-Aided Design Of Skeletal Implants," which is incorporated by reference in its entirety, discloses methods for production of an implant for a patient prior to an operation. The invention comprises the steps of generating data from a three-dimensional scan of the patient's defect site and fabricating the implant based on the implant design data generated on a computer.

SUMMARY OF THE INVENTION

An aspect of the invention is directed to methods of manufacturing shaped biomaterial-based implants via a three-dimensional printing step. The shaped biomaterial-based implants comprise a three-dimensional form of selected dimensions. The properties of the biomaterial-based implants include biocompatibility, a surface for cellular infiltration, interconnected porosity, access to an infinite variety of shapes and sizes, and combinations thereof. The methods of manufacturing the shaped biomaterial-based implants rely on judicious selection of biomaterial and binding agents. In some embodiments, the biomaterial-based implants are suitable for implantation into a patient.

An aspect of the invention is a method of generating a three-dimensional biomaterial-based implant. The method includes visualizing the implantation site and producing a mold of the dimensions of the implantation site using three-dimensional printing technology. The three-dimensional biomaterial-based implant is produced in the mold. The implant is made of a biomaterial and is substantially the dimensions of the implantation site.

An aspect of the invention is a method of generating a three-dimensional biomaterial-based implant. The method includes visualizing the implantation site to produce a three-dimensional biomaterial based implant comprising a biomaterial to the dimensions of the implantation site.

An aspect of the invention is a method of three-dimensional printing a biomaterial-based implant. Biomaterial and a binding agent are combined within a three-dimensional printer. The printer is used to create the implant of desired dimensions.

An aspect of the invention is a method of generating a three-dimensional biomaterial implant by three-dimensional printing of a biomaterial to form an implant of desired dimensions.

DETAILED DESCRIPTION OF THE INVENTION

Figure 1:
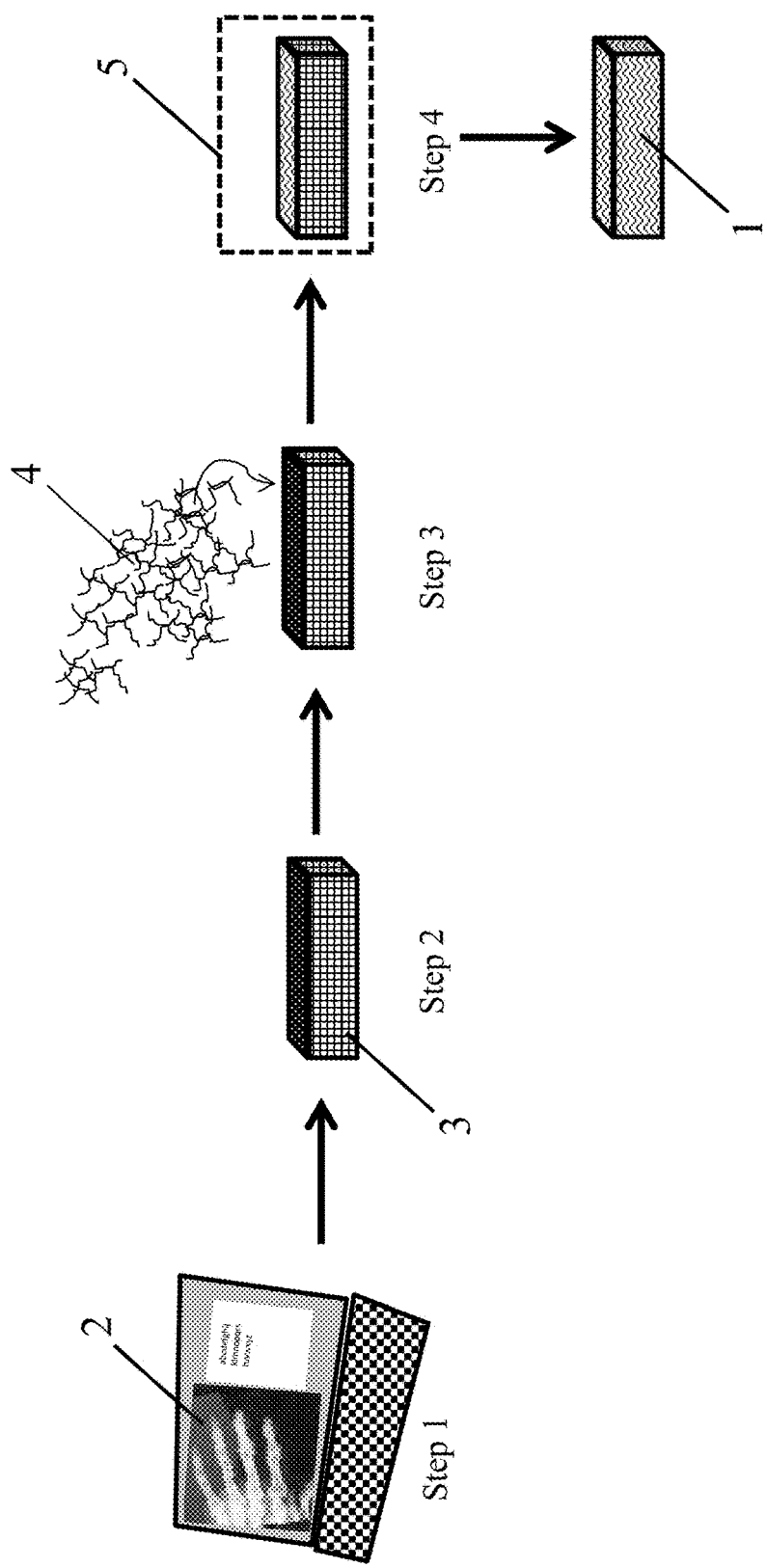
FIG. 1 illustrates a method to form shaped biomaterial-based implants via a three-dimensional printed mold.

The invention relates to shaped, biomaterial-based implants and methods of producing the shaped, biomaterial-based implants.

"Three-dimensional printing technology", as used herein, refers to a variety of additive manufacturing processes for making a three-dimensional object based on a three-dimensional model or electronic source input under computer control.

"Allogeneic" or "allograft", as used herein, refers to tissue derived from a non-identical donor of the same species.

"Autogeneic" or "autograft", as used herein, refers to tissue derived from and implanted into the same identical patient.

"Biocompatible" as used herein, refers to the property of being biologically compatible with a living being by not producing harm.

"Biomaterial" as used herein, includes plant or animal derived tissues. In some embodiments, the biomaterial may be animal derived cortical bone, cancellous bone, connective tissue, tendon, pericardium, dermis, cornea, dura matter, fascia, heart valve, ligament, capsular graft, cartilage, collagen, nerve, placental tissue, or combinations thereof. In some embodiments, the biomaterial-based implants can be formed from demineralized bone matrix (DBM) material.

"Osteoinductive", as used herein, refers to the ability of a material to induce bone healing via recruitment of osteoprogenitor cells.

"Patient" as used herein, refers to a living recipient of the shaped, biomaterial-based implants of the present invention.

"Xenogeneic" or "xenograft" as used herein, is defined as tissue derived from a non-identical donor of a different species.

The shaped biomaterial-based implants may be sponge-like materials, which may be used as scaffolding for tissue ingrowth following implantation into a patient. Furthermore, while the invention may be used to produce a biomaterial-based sheet that may later be cut to form a specific shape, the invention allows the shaped biomaterial-based implants to be formed without an additional cutting step.

The shaped biomaterial-based implants of the invention have many advantages over the prior art. The hydrated biomaterial-based products of the invention compress under a force of between about 10 g-force/square cm to about 4000 g-force/square cm. In some embodiments, the force applied to compress the biomaterial-based products may be at least about 10 g-force/square cm, 100 g-force/square cm, 500 g-force/square cm, 1000 g-force/square cm, 2000 g-force/square cm, 3000 g-force/square cm, or 3500 g-force/square cm. The shaped biomaterial-based product may be compressible to between about 5% of its original size to about 80% of its original size. In some embodiments, the shaped biomaterial-based product may be compressible to about 80% of its original size, to about 60% of its original size, to about 20% of its original size, to about 5% of its original size. In some embodiments, the biomaterial-based implants may be formed from DBM with a residual calcium level of between about 0% to about 8%. In some embodiments, the residual calcium level may be about 8%, about 6%, about 4%, about 2% and about 0%.

An aspect of the invention is a method of generating a three-dimensional biomaterial-based implant. The method includes visualizing an implantation site and producing a mold of the dimensions of the implantation site utilizing three-dimensional printing technology. The three-dimensional biomaterial-based implant is produced in the mold. The implant includes a biomaterial and the size of the implant corresponds with the dimensions of the implantation site.

In some embodiments of the invention, the visualization step can be performed with an imaging tool, which includes but is not limited to, of X-ray, ultrasound, CT imaging, MRI imaging, and combinations thereof. The visualization of the implantation site can occur by imaging multiple implantation sites in multiple patients and taking an average of the dimensions of the implantation site. As the implantation site and dimensions can depend on the patient, the visualization of the implantation site can be imaged for a single patient. In some embodiments, multiple patients can provide a representative image and dimensions of an implantation site. In some embodiments, the results of the visualization of an implantation site in multiple patients can be used to determine dimensions of a mold in some composite analysis, such as determining an average dimension or a maximum or minimum dimension of the implantation site. The patient or patients can be any animal, including a human.

The material of the three-dimensional biomaterial-based implant can be powder, fibers, particles, shards, strips, or combinations thereof. The biomaterial can include bone, connective tissue, tendon, pericardium, dermis, cornea, dura matter, fascia, heart valve, ligament, capsular graft, cartilage, collagen, nerve, placental tissue, and combinations thereof. In some embodiments when the biomaterial is bone, the bone material can be cortical bone, cancellous bone or combination thereof. The bone can be mineralized, fully demineralized, partially demineralized, or a combination of the foregoing. Demineralized bone matrix (DBM) for use by the disclosed method may be prepared using any method or techniques known in the art, for a typical demineralization protocol, for example U.S. Pat. No. 5,314,476, or 8,574,825, each of which is incorporated in their entirety by reference. The implantation site can be any skeletal site, including but not limited to, extremity defects, cranial defects, craniomaxillofacial defects, and spinal voids.

The dimensions of the biomaterial-based implants can depend upon the final use of the implant. In some embodiments, the dimensions can range in thickness from between about 0.1 mm to 50 mm, between about 0.3 mm to 40 mm, or between about 0.5 to 30 mm. The length of the implants may range from between about 5 mm to 25 cm, between about 10 mm to 20 cm, or between about 10 mm to 10 cm. The width of the implants may range from between about 5 mm to 25 cm, between about 10 mm to 20 cm, or between about 10 mm to 10 cm. In some embodiments, the final dimension of the implant can have a slightly larger from the dimensions of the implant to ensure full contact within the implantation site. In some embodiments, at least one dimension of the implant can be within a tolerance of +/− about 0.01 mm of at least one dimension of the implantation site.

A material for the mold can be any suitable material, including but not limited to, ceramics, elastomers, aluminum, stainless steel, thermoplastics, or combinations thereof. The mold can be amenable to steam sterilization. The mold can be constructed of a screen-like material or may include at least one drain hole on at least one side of the mold to allow fluid to enter or exit the interior cavity of the mold. The mold can have a non-stick coating, such as Teflon. A lid can be used with the mold. The mold or mold lid can apply adjustable inward pressure upon the biomaterials during shaping.

A computer-aided design (CAD) software program can be used to operate or provide dimensions to the 3-D printer.

The binding agent can be any suitable binding material, including but not limited to, a glue, a gum, a sugar, a polysaccharide, a cellulose ether, a resin, and combinations thereof. The three dimensional printing process can, but is not limited to, fused filament fabrication, plaster-based three-dimensional printing, selective laser sintering, selective heat sintering, direct ink writing, and combinations thereof.

An additive can be included in and/or on the implant. The additive can be added during manufacturing or after the implant has been formed. Suitable additives include, but are not limited to, silver sulfadiazine, chlorhexidine, gentamicin, tobramycin, vancomycin and combinations thereof.

After the three-dimensional biomaterial-based implant has been produced, it can be milled in order to adjust one or more dimension. A three-dimensional printer can be used to further mill the implant.

An aspect of the invention is a method of generating a three-dimensional biomaterial-based implant. The method includes visualizing an implantation site and producing an implant of the dimensions of the implantation site utilizing three-dimensional printing technology. The three-dimensional biomaterial-based implant is produced by printing the biomaterial to the dimensions of the implantation site.

In some embodiments of the invention, the visualization step can be performed with an imaging tool, which includes but is not limited to, of X-ray, ultrasound, CT imaging, MRI imaging, and combinations thereof. The visualization of the implantation site can occur by imaging multiple implantation sites in multiple patients and taking an average of the dimensions of the implantation site. As the implantation site and dimensions can depend on the patient, the visualization of the implantation site can be imaged for a single patient. In some embodiments, multiple patients can provide a representative image and dimensions of an implantation site. The patient or patients can be any animal, including a human.

The implant can be made using any suitable method. By way of example only, U.S. patent application Ser. No.

14/639,902, which has been incorporated by reference, discloses a method to produce a bone body. The implant can be any suitable shape, including but not limited to, a block, cylinder, pyramid, sphere, dome, capped sphere, cone, cuboids, prism, and hexagonal prism. The material of the implant can be powder, fibers, particles, shards, strips, or combinations thereof. The implant can include bone, connective tissue, tendon, pericardium, dermis, cornea, dura matter, fascia, heart valve, ligament, capsular graft, cartilage, collagen, nerve, placental tissue, and combinations thereof. In some embodiments when the implant is bone, the bone material can be cortical bone, cancellous bone or combination thereof. The bone can be mineralized, fully demineralized, partially demineralized, or a combination of the foregoing. Demineralized bone matrix (DBM) for use by the disclosed method may be prepared using any method or techniques known in the art, for a typical demineralization protocol, for example U.S. Pat. No. 5,314,476, or 8,574,825, each of which is incorporated in their entirety by reference.

The three-dimensional biomaterial-based implant can further include an additive. Suitable additives include, but are not limited to, bioactive agents, growth factors, hormones, cells, antibiotics, biocompatible minerals, antimicrobials, or combinations thereof. The biomaterial used to produce the bone block can be of lengths of between about 1 mm to about 200 mm, between about 2 mm to about 150 mm, between about 5 mm to about 70 mm, or between about 10 mm to about 60 mm. The biomaterials may have diameters of between about 0.1 mm to about 30 mm, between about 0.2 mm to about 15 mm, between about 0.5 mm to about 10 mm, or between about 1 mm to about 8 mm. The bone for the present invention may be generated by a variety of methods and techniques known in the prior art, for example U.S. Pat. No. 5,314,476, which is incorporated in its entirety by reference.

The implantation site can be any skeletal site, including but not limited to, extremity defects, cranial defects, craniomaxillofacial defects, and spinal voids.

The dimensions of the biomaterial-based implants can depend upon the final use of the implant. In some embodiments, the dimensions can range in thickness from between about 0.1 mm to 50 mm, between about 0.3 mm to 40 mm, or between about 0.5 to 30 mm. The length of the implants may range from between about 5 mm to 25 cm, between about 10 mm to 20 cm, or between about 10 mm to 10 cm. The width of the implants may range from between about 5 mm to 25 cm, between about 10 mm to 20 cm, or between about 10 mm to 10 cm. In some embodiments, at least one dimension of the implant can be within a tolerance of +/− about 0.01 mm of at least one dimension of the implantation site.

A material for the mold can be any suitable material, including but not limited to, ceramics, elastomers, aluminum, stainless steel, thermoplastics, or combinations thereof. The mold can be amenable to steam sterilization. The mold can be constructed of a screen-like material or may include at least one drain hole on at least one side of the mold to allow fluid to enter or exit the interior cavity of the mold. The mold can have a non-stick coating, such as Teflon. A lid can be used with the mold. The mold or mold lid can apply adjustable inward pressure upon the biomaterials during shaping.

An additive can be included in and/or on the implant. The additive can be added during manufacturing or after the implant has been formed. Suitable additives include, but are not limited to, silver sulfadiazine, chlorhexidine, gentamicin, tobramycin, vancomycin and combinations thereof.

A computer-aided design (CAD) software program can be used to operate or provide dimensions to the 3-D printer.

The binding agent can be any suitable binding material, including but not limited to, a glue, a gum, a sugar, a polysaccharide, a cellulose ether, a resin, and combinations thereof. The three dimensional printing process can, but is not limited to, fused filament fabrication, plaster-based three-dimensional printing, selective laser sintering, selective heat sintering, direct ink writing, and combinations thereof.

An aspect of the invention is a method of three-dimensional printing a biomaterial-based implant. The method includes combining a biomaterial and a binding agent within a three-dimensional printer and printing the implant of desired dimensions. The implant can be printed onto or into a separate medical implant or on a medical device. The implant can fully encapsulate, or partially cover the medical implant or medical device. The hybrid of the implant material and the medical implant or device can be used in other applications. For example, a hybrid implant can be implanted into a patient.

The material of the biomaterial can be powder, fibers, particles, shards, strips, or combinations thereof. The biomaterial can include bone, connective tissue, tendon, pericardium, dermis, cornea, dura matter, fascia, heart valve, ligament, capsular graft, cartilage, collagen, nerve, placental tissue, and combinations thereof. In some embodiments when the biomaterial is bone, the bone material can be cortical bone, cancellous bone or combination thereof. The bone can be mineralized, fully demineralized, partially demineralized, or a combination of the foregoing. Demineralized bone matrix (DBM) for use by the disclosed method may be prepared using any method or techniques known in the art, for a typical demineralization protocol, for example U.S. Pat. No. 5,314,476, or 8,574,825, each of which is incorporated in their entirety by reference.

The binding agent can be any suitable binding material, including but not limited to, a glue, a gum, a sugar, a polysaccharide, a cellulose ether, a resin, and combinations thereof. The three dimensional printing process can, but is not limited to, fused filament fabrication, plaster-based three-dimensional printing, selective laser sintering, selective heat sintering, direct ink writing, and combinations thereof. Furthermore, selective heat sintering or selective laser sintering can be used to shape the implant during or after it has been attached to the medical implant or medical device.

Solvents can be combined with the biomaterial in the presence or absence of the binding agents to facilitate three-dimensional printing. The solvents can include, but are not limited to, water, alcohols, biocompatible organic solvents, buffers, or combinations thereof. Suitable biocompatible organic solvents include, but are not limited to, acetonitrile, dimethyl sulfoxide, acetone, ethyl acetate or combinations thereof. Suitable alcohols include, but are not limited to, ethanol, isopropanol, methanol or combinations thereof. Suitable buffers include, but are not limited to, Hank's balanced salt solution, phosphate buffered saline, saline or combinations thereof.

An additive can be included in and/or on the implant. The additive can be added during manufacturing or after the implant has been formed. Suitable additives include, but are not limited to, silver sulfadiazine, chlorhexidine, gentamicin, tobramycin, vancomycin and combinations thereof.

An aspect of the invention is a method of generating a three-dimensional biomaterial implant by three-dimensional printing of a biomaterial to form an implant of desired dimensions.

The biomaterial particles, pieces, strips, or fibers used for forming the shaped biomaterial-based implants may be of lengths of between about 1 mm to about 200 mm, or any length or range within this range, including a range between about 2 mm to about 150 mm, between about 5 mm to about 70 mm, or between about 10 mm to about 60 mm. The biomaterials may have diameters of between about 0.1 mm to about 30 mm, between about 0.2 mm to about 15 mm, between about 0.5 mm to about 10 mm, or between about 1 mm to about 8 mm. When the shaped biomaterial-based implants 1 are comprised of bone, the bone may be cortical, cancellous, or a combination of the two bone types. The bone for the present invention may be generated by a variety of methods and techniques known in the prior art, for example U.S. Pat. No. 5,314,476, which is incorporated in its entirety by reference. The bone comprising the shaped biomaterial-based implants 1 may be mineralized, fully demineralized, partially demineralized, or a combination of the foregoing. Demineralized bone matrix (DBM) for use by the disclosed method may be prepared using any method or techniques known in the art, for a typical demineralization protocol, for example U.S. Pat. No. 5,314,476, or 8,574,825, each of which is incorporated in their entirety by reference.

FIG. 1 illustrates a method of forming shaped biomaterial-based implants 1. Step 1 illustrates visualization 2 of an implantation site in or on a patient's body. The patient may be any animal, and preferably a human. An implantation site may be visualized by imaging, drawing, modeling, or combinations of visualization methods. Medical imaging techniques include, but are not limited to, x-ray fluoroscopy, magnetic resonance imaging, CT scanning, and ultrasound imaging. In some embodiments, the visualization of the implantation site may occur by imaging multiple implantation sites in multiple patients and averaging the dimensions of the implantation site. In some embodiments, the visualization of the implantation site, Step 1, may be omitted. In embodiments without a visualization step, the dimensions of the implant may be selected from various implant sizes. Implant sizes may vary based on the common sizes required for a particular implantation. For example, an implant of the dimensions about 50 mm by about 5 mm by about 5 mm may be selected for implantation. If the implant dimensions are slightly over-sized, the implant may be reduced in size by trimming, compression, or other treatment by the end user. Alternatively, if an implant of a specific size is selected and found to be too small for the implantation site, another or multiple other implants of suitable size may be used in addition to the first implant selected.

Following visualization 2 of the implantation site, the desired dimensions of the implant may be selected to fit the visualized implantation site and entered into a computer-aided design (CAD) software program. Optionally, the visualization step of the method may be omitted, and the desired implant dimensions may be entered into a CAD software program. Once the desired implant dimensions are entered into a CAD software program, a mold 3 may be three-dimensional printed to the implant dimension specification. Using the mold 3, a biomaterial 4 or biomaterial mixture may be added to the mold as shown in Step 3 of FIG. 1. The mold 3 is capable of forming a three-dimensional shape. In some embodiments, the mold 3 may fully enclose the biomaterial, or may have a lid if desired. The lid may be attached to the mold, detachable, or separate from the mold. The mold 3 and lid may be perforated to fully or partially to allow curing of the biomaterial 4 during shaping. In other embodiments, the mold may be used to form a three-dimensional shape, for example, a sheet of material, which may be further shaped. The mold 3 may be composed of various heat resistant materials such as, but not limited to, ceramics, elastomers, aluminum, stainless steel, thermoplastics, or combinations thereof. The mold 3 may be amenable to steam sterilization. The mold 3 may be constructed of a screen-like material. The mold 3 may have a non-stick coating, such as Teflon. The mold 3 or mold lid may apply adjustable inward pressure upon the biomaterials during shaping.

In some embodiments, the mold 3 may have drainage holes or openings to allow moisture and chemicals to enter and exit the product during use. In some embodiments, the mold 3 may have openings or drainage holes at least on one side. In other embodiments, the mold 3 may comprise only three sides so that moisture may exit from open sides of the mold 3. In other embodiments, the mold 3 may be composed of a screen with numerous openings to allow fluid entry or exit during use. In other embodiments, the mold 3 may be a sieve or strainer. After the biomaterial 4 is shaped within the mold 3, it may be cured, dried, lyophilized, or chemically treated in some manner 5 to retain the shape of the inner mold 3 dimensions. For example, suitable methods of dehydration of demineralized bone fibers to form implants of the present invention may be found in U.S. patent application Ser. No. 14/639,902 which is incorporated in its entirety by reference. After the shaping process of Step 4, the biomaterial-based implant 1 may be removed from the mold 3 and used for implantation into a patient. The shaped biomaterial-based implants 1 may be shaped in the form of a block as shown in FIG. 1, or in the form of a cube, strip, sphere, sheet, or other three-dimensional shape as desired. The shape of the product may be uniform or irregular as desired. In some embodiments, the biomaterial-based implant 1 may remain within the mold 3. In further embodiments, the final biomaterial-based implant 1 may remain partially or fully attached to the mold 3. Implants composed of the biomaterial and the complete or partial mold may be used as an intact unit for implantation within a patient. In such embodiments, the mold 3 serves the additional role of a medical implant, e.g., a spinal cage implant.

Figure 2:
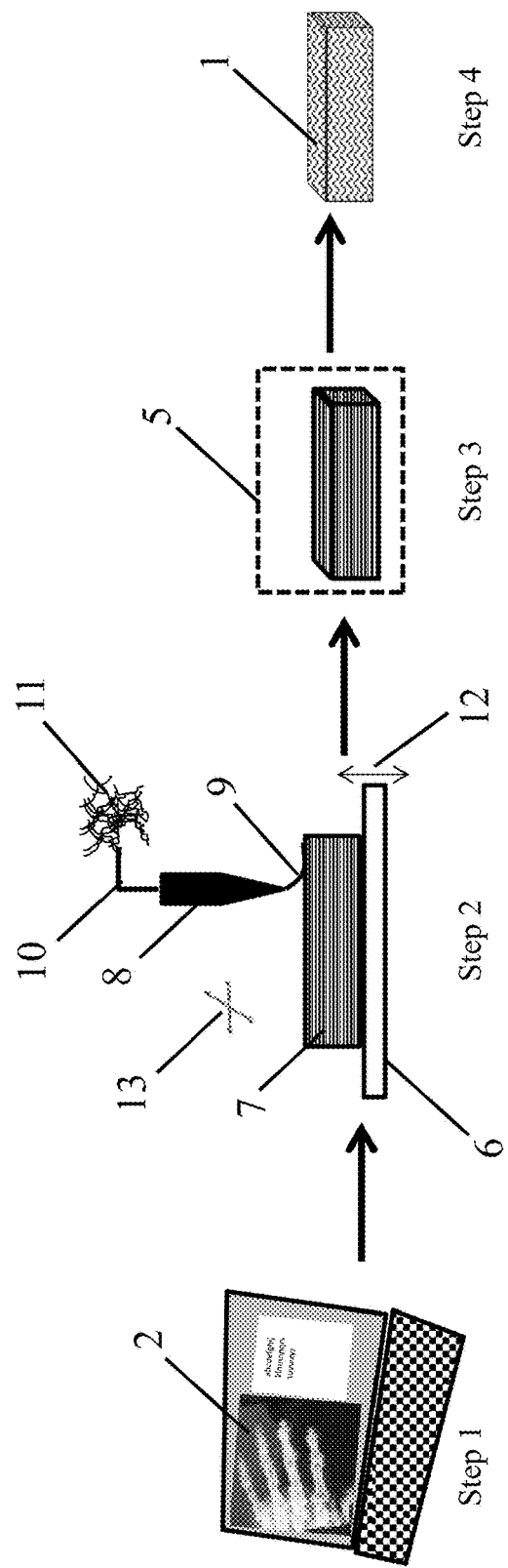
FIG. 2 illustrates a method to form shaped biomaterial-based implants via three-dimensional printing of the implants.

FIG. 2 illustrates an alternative method of forming shaped biomaterial-based implants 1. As shown in FIG. 1, Step 1 comprises visualization of the implantation site in or on a patient's body. In some embodiments, the visualization of the implantation site, Step 1, may be omitted. In embodiments without a visualization step, the dimensions of the implant may be selected from various implant sizes. Implant sizes may vary based on the common sizes required for a particular implantation. The desired dimensions of the implant may then be entered into a CAD software program to enable the three-dimensional printing of the biomaterial-based implant 1. The three-dimensional printing may take place on a movable 12 platform 6. Above the platform a movable 13 extrusion head 8 may deliver the semi-solid 9 biomaterial mixture to be shaped and hardened 7 on the platform 6. The biomaterial 11 may be prepared into a mixture 10, which may be fed into the extrusion head 8 during the three-dimensional printing. The biomaterial may be in a melted form, powdered state, or other micronized form. In other embodiments, the three-dimensional printing may utilize selective heat sintering (SHS) or selective laser sintering (SLS) to shape the implant. If SHS or SLS are used, the three-dimensional printing may take place on a movable 12 platform 6. As the biomaterial 11 or the biomaterial mixture 10 is layered onto the implant platform, heat or laser power may be used to control the thermal binding of the biomaterial 11 or biomaterial mixture 10 into the final three-dimensional shaped implant. Binding agents may be combined with the biomaterial 11 into the mixture 10 to provide a biomaterial-based implant of the desired physical properties and cohesiveness.

The three-dimensional printing of the biomaterial 11 may be used to fully or partially coat the surface of a medical implant. In some embodiments, a medical implant may be affixed onto the movable platform 6. During the three-dimensional printing process, the biomaterial 11 may be directly three-dimensional printed onto a medical implant. In this manner, medical implants may be fully or partially coated with biomaterial. In some embodiments, the medical implant affixed to the movable platform 6 may be attached in multiple orientations, as desired, in order to allow three-dimensional printing on multiple sides and aspects of the medical implant. These hybrid medical implant/biomaterial printed units may then be implanted directly within a patient.

Suitable binding agents may be polymers, glues, gums, sugars, cellulose ethers, resins, or combinations thereof. Solvents may be combined with the biomaterial in the presence or absence of the binding agents to facilitate three-dimensional printing. The solvents may include water, alcohols, biocompatible organic solvents, buffers, or combinations thereof. Suitable biocompatible organic solvents include, but are not limited to, acetonitrile, dimethyl sulfoxide, acetone, ethyl acetate or combinations thereof. Suitable alcohols include, but are not limited to, ethanol, isopropanol, methanol or combinations thereof. Suitable buffers include, but are not limited to, Hank's balanced salt solution, phosphate buffered saline, saline or combinations thereof.

The biomaterial particles, pieces, strips, or fibers used for forming the shaped biomaterial-based implants may be of lengths of between about 1 mm to about 200 mm, between about 2 mm to about 150 mm, between about 5 mm to about 70 mm, or between about 10 mm to about 60 mm. The biomaterials may have diameters of between about 0.1 mm to about 30 mm, between about 0.2 mm to about 15 mm, between about 0.5 mm to about 10 mm, or between about 1 mm to about 8 mm. When the shaped biomaterial-based implants 1 are comprised of bone, the bone may be cortical, cancellous, or a combination of the two bone types. The bone for the present invention may be generated by a variety of methods and techniques known in the prior art, for example U.S. Pat. No. 5,314,476, which is incorporated in its entirety by reference. The bone comprising the shaped biomaterial-based implants 1 may be mineralized, fully demineralized, partially demineralized, or a combination of the foregoing. Demineralized bone matrix (DBM) for use by the disclosed method may be prepared using any method or techniques known in the art, for a typical demineralization protocol, for example U.S. Pat. No. 5,314,476, or 8,574,825, each of which is incorporated in their entirety by reference.

Three-dimensional biomaterial-based implants may range in thickness from between about 0.1 mm to 50 mm, between about 0.3 mm to 40 mm, or between about 0.5 to 30 mm. The length of the implants may range from between about 5 mm to 25 cm, between about 10 mm to 20 cm, or between about 10 mm to 10 cm. The width of the implants may range from between about 5 mm to 25 cm, between about 10 mm to 20 cm, or between about 10 mm to 10 cm.

The foregoing description of the invention has been presented for illustration and description purposes. However, the description is not intended to limit the invention to only the forms disclosed herein. In the foregoing Detailed Description for example, various features of the invention are grouped together in one or more embodiments for the purpose of streamlining the disclosure. This method of disclosure is not to be interpreted as reflecting an intention that the claimed invention requires more features than are expressly recited in each claim. Rather, as the following claims reflect, inventive aspects lie in less than all features of a single foregoing disclosed embodiment. Thus, the following claims are hereby incorporated into this Detailed Description, with each claim standing on its own as a separate preferred embodiment of the invention.

Consequently, variations and modifications commensurate with the above teachings and skill and knowledge of the relevant art are within the scope of the invention. The embodiments described herein above are further intended to explain best modes of practicing the invention and to enable others skilled in the art to utilize the invention in such a manner, or include other embodiments with various modifications as required by the particular application(s) or use(s) of the invention. Thus, it is intended that the claims be construed to include alternative embodiments to the extent permitted by the prior art.

What is claimed:

1. A method of generating a three-dimensional biomaterial-based implant, comprising:
   visualizing an implantation site;
   producing a mold comprising dimensions of the implantation site by three-dimensional printing;
   placing a biomaterial in the mold wherein a shape of the biomaterial is at least one of a fiber, a shard, and a strip;
   applying a pressure to the biomaterial in the mold; and
   drying the biomaterial in the mold to form the biomaterial-based implant, wherein the void to fiber ratio of the implant is between about 1:99 to about 1:11, wherein the drying step heats the mold to a temperature between about 30° C. to about 80° C.; and
   incorporating a separate medical implant and the biomaterial-based implant.

2. The method of claim 1, wherein the visualization is selected from at least one of X-ray, ultrasound, CT imaging, and MRI imaging.

3. The method of claim 1, wherein the visualization of the implantation site comprises imaging implantation sites in multiple patients.

4. The method of claim 3, wherein the imaging multiple implantation sites in the multiple patients provides a representative image of an implantation site type.

5. The method of claim 1, wherein the visualization of the implantation site occurs by imaging the implantation site of a single patient.

6. The method of claim 1, wherein the biomaterial comprises at least two materials selected from the group consisting of a bone, a connective tissue, a tendon, a pericardium, a dermis, a cornea, a dura matter, a fascia, a heart valve, a ligament, a capsular graft, a cartilage, a collagen, a nerve, a placental tissue, and combinations thereof.

7. The method of claim 6, wherein the biomaterial is the bone and wherein the bone material is at least one of cortical, cancellous or a combination thereof.

8. The method of claim 6, wherein the biomaterial is the bone, and wherein the bone is at least one of demineralized, partially demineralized, or fully mineralized.

9. The method of claim 1, wherein at least one additive is included with the biomaterial within the mold.

10. The method of claim 1, further comprising contacting the biomaterial in the mold with a binding agent selected from the group consisting of a glue, a gum, a sugar, a polysaccharide, a cellulose ether, a resin, and combinations thereof.

11. The method of claim 1, wherein the biomaterial is around a separate material within the mold.

12. The method of claim 11, wherein the separate material is biocompatible.

13. The method of claim 1, wherein the biomaterial further comprises a second shape of at least one of a powder and a particle.

14. A method of generating a three-dimensional biomaterial-based implant, comprising:
visualizing an implantation site; and
producing the three-dimensional biomaterial-based implant comprising a biomaterial to the dimensions of the implantation site, wherein a shape of the biomaterial of the three-dimensional biomaterial-based implant is at least one of a powder, a fiber, a particle, a shard, and a strip, wherein a material of the biomaterial is selected from the group consisting of a bone, a connective tissue, a tendon, a pericardium, a dermis, a cornea, a dura matter, a fascia, a heart valve, a ligament, a capsular graft, a cartilage, a collagen, a nerve, a placental tissue, and combinations thereof, wherein the implant is compressible to between about 5% of its original size to about 80% of its original size, and wherein the biomaterial-based implant further comprises a separate medical implant.

15. The method of claim 14, wherein the visualization is selected from at least one of X-ray, ultrasound, CT imaging, and MM imaging.

16. The method of claim 14, wherein the visualization of the implantation site comprises imaging implantation sites in multiple patients.

17. The method of claim 16, wherein the imaging of the multiple implantation sites in the multiple patients provides a representative image of the implantation site.

18. The method of claim 14, wherein the visualization of the implantation site comprises imaging the implantation site of a single patient.

19. The method of claim 14, wherein the producing of the three-dimensional biomaterial-based implant comprises three-dimensional printing the implant.

20. The method of claim 14, wherein the biomaterial is bone and wherein the bone material is at least one of a cortical bone, or a cancellous bone.

21. The method of claim 14, wherein the biomaterial is the bone, and wherein the bone is at least one of a demineralized bone, partially demineralized bone, or fully mineralized bone.

22. A method of forming a biomaterial-based implant, comprising:
combining a biomaterial and a binding agent in a three-dimensional printer to form a combined material; and
printing the combined material to create an implant of desired dimensions, wherein the biomaterial-based implant is three-dimensionally printed into a separate medical implant in order to be implanted into a patient as a hybrid implant unit.

23. The method of claim 22, wherein the biomaterial is selected from the group consisting of bone, connective tissue, tendon, pericardium, dermis, cornea, dura matter, fascia, heart valve, ligament, capsular graft, cartilage, collagen, nerve, placental tissue, and combinations thereof.

24. The method of claim 22, wherein the binding agent is selected from the group including a glue, a gum, a sugar, a polysaccharide, a cellulose ether, a resin, and combinations thereof.

25. The method of claim 22, wherein the three-dimensional printing process is selected from the group consisting of fused filament fabrication, plaster-based three-dimensional printing, selective laser sintering, selective heat sintering, and direct ink writing.

* * * * *